(12) United States Patent
Penenberg

(10) Patent No.: US 10,390,846 B2
(45) Date of Patent: *Aug. 27, 2019

(54) APPARATUS FOR AND METHOD OF PROVIDING A HIP REPLACEMENT

(71) Applicant: MICROPORT ORTHOPEDICS HOLDINGS INC., Tiel (NL)

(72) Inventor: Brad L. Penenberg, Beverly Hills, CA (US)

(73) Assignee: MicroPort Orthopedics Holdings Inc., Tiel (NL)

( * ) Notice: Subject to any disclaimer, the term of this patent is extended or adjusted under 35 U.S.C. 154(b) by 482 days.

This patent is subject to a terminal disclaimer.

(21) Appl. No.: 14/282,750

(22) Filed: May 20, 2014

(65) Prior Publication Data

US 2015/0335337 A1    Nov. 26, 2015

(51) Int. Cl.
*A61B 17/17* (2006.01)
*A61F 2/46* (2006.01)
(Continued)

(52) U.S. Cl.
CPC ...... *A61B 17/1746* (2013.01); *A61B 17/1666* (2013.01); *A61F 2/4607* (2013.01); *A61F 2/4609* (2013.01); *A61F 2/4657* (2013.01); *A61B 17/00234* (2013.01); *A61B 17/1668* (2013.01); *A61B 17/175* (2013.01); *A61B 17/92* (2013.01); *A61B 2017/0046* (2013.01); *A61B 2017/3405* (2013.01); *A61B 2090/395* (2016.02); *A61B 2090/3908* (2016.02);
(Continued)

(58) Field of Classification Search
CPC ........ A61B 2018/2025; A61B 17/1666; A61B 17/1746

See application file for complete search history.

(56) References Cited

U.S. PATENT DOCUMENTS

| 3,685,058 A | 8/1972 | Tronzo |
| 3,859,992 A | 1/1975 | Amstulz |

(Continued)

FOREIGN PATENT DOCUMENTS

| CA | 2343926 A1 | 10/2001 |
| EP | 0147339 A2 | 7/1985 |

(Continued)

*Primary Examiner* — Zade Coley

(57) ABSTRACT

A short main incision and portal incisions at portal positions strategically displaced from the main incision are provided in a patient's hip. One portal incision (acetabular portal) provides for a disposition of reamers in the patient's acetabulum to shape the acetabulum. A cannula is inserted through the portal incision to the acetabulum and the successive reamers of progressive size are inserted into the acetabulum through the main incision to progressively size and shape the acetabulum. An approximately hemispherical acetabular component is then disposed in the prepared acetabulum to provide for hip rotation relative to the femoral component. The other portal incision (femoral portal) provides for insertion into the patient's hip of a member for driving the femoral stem into a cavity in the patient's femur. The provision of the short main incision and the portal incision minimizes the patient's loss of blood, tissue trauma, length of operating time and patient recovery time.

20 Claims, 6 Drawing Sheets

(51) Int. Cl.
*A61B 17/16* (2006.01)
*A61B 17/92* (2006.01)
*A61B 17/00* (2006.01)
*A61B 17/34* (2006.01)
*A61F 2/34* (2006.01)
*A61F 2/36* (2006.01)
*A61B 90/00* (2016.01)

(52) U.S. Cl.
CPC . *A61F 2/34* (2013.01); *A61F 2/36* (2013.01); *A61F 2/3662* (2013.01); *A61F 2/4684* (2013.01); *A61F 2002/4635* (2013.01); *A61F 2002/4681* (2013.01)

(56) References Cited

U.S. PATENT DOCUMENTS

| | | | |
|---|---|---|---|
| 3,874,003 A | 4/1975 | Moser et al. | |
| 4,305,394 A | 12/1981 | Bertuch, Jr. | |
| 4,399,813 A | 8/1983 | Barber | |
| 4,475,549 A | 10/1984 | Oh | |
| 4,528,980 A | 7/1985 | Kenna | |
| 4,632,111 A | 12/1986 | Roche | |
| 4,662,891 A | 5/1987 | Noiles | |
| 4,677,972 A | 7/1987 | Tornier | |
| 4,716,894 A | 1/1988 | Lazzeri et al. | |
| 4,865,025 A | 9/1989 | Buzzi et al. | |
| 4,878,918 A | 11/1989 | Tari et al. | |
| 4,994,064 A | 2/1991 | Aboczky | |
| 5,030,221 A | 7/1991 | Buechel et al. | |
| 5,037,424 A | 8/1991 | Aboczky | |
| 5,061,270 A | 10/1991 | Aboczky | |
| 5,098,437 A | 3/1992 | Kashuba et al. | |
| 5,108,448 A | 4/1992 | Gautier | |
| 5,108,452 A | 4/1992 | Fallin | |
| 5,116,339 A | 5/1992 | Glock | |
| D331,461 S | 12/1992 | Lester | |
| 5,169,399 A | 12/1992 | Ryland et al. | |
| 5,171,243 A | 12/1992 | Kashuba et al. | |
| 5,171,313 A | 12/1992 | Salyer | |
| 5,190,422 A | 3/1993 | Lechot | |
| 5,217,499 A | 6/1993 | Shelley | |
| 5,250,051 A | 10/1993 | Maryan | |
| 5,261,915 A | 11/1993 | Durlacher et al. | |
| 5,284,483 A | 2/1994 | Johnson et al. | |
| 5,320,625 A | 6/1994 | Bertin | |
| 5,344,461 A | 9/1994 | Philpot | |
| 5,364,403 A | 11/1994 | Petersen et al. | |
| 5,417,696 A | 5/1995 | Kashuba | |
| 5,458,637 A | 10/1995 | Hayes | |
| 5,474,560 A | 12/1995 | Rohr, Jr. | |
| 5,486,181 A | 1/1996 | Cohen et al. | |
| 5,499,985 A | 3/1996 | Hein et al. | |
| 5,507,748 A | 4/1996 | Sheehan et al. | |
| 5,637,074 A * | 6/1997 | Andino | A61B 17/3403 |
| | | | 128/DIG. 25 |
| 5,658,290 A | 8/1997 | Lechot | |
| 5,683,399 A | 11/1997 | Jones | |
| 5,814,050 A | 9/1998 | Benson | |
| 5,891,158 A | 4/1999 | Manwaring et al. | |
| 5,904,688 A | 5/1999 | Gilbert | |
| 5,928,287 A | 7/1999 | Keller | |
| 5,968,049 A | 10/1999 | DaRold | |
| 6,063,123 A | 5/2000 | Burrows et al. | |
| 6,063,124 A | 5/2000 | Amstutz | |
| 6,106,536 A | 8/2000 | Lechot | |
| 6,129,732 A | 10/2000 | Lechot | |
| 6,132,469 A | 10/2000 | Schroeder | |
| 6,254,604 B1 | 7/2001 | Howell | |
| 6,264,647 B1 | 7/2001 | Lechot | |
| 6,371,124 B1 | 4/2002 | Whelan | |
| 6,482,209 B1 | 11/2002 | Engh et al. | |
| 6,626,913 B1 | 9/2003 | McKinnon et al. | |
| 6,676,706 B1 | 1/2004 | Mears | |
| 6,695,850 B2 * | 2/2004 | Diaz | A61B 17/1631 |
| | | | 606/91 |
| 6,905,502 B2 | 6/2005 | Penenberg | |
| 7,833,229 B2 | 11/2010 | Penenberg | |
| 2001/0006593 A1 | 7/2001 | Lechot | |
| 2002/0002365 A1 | 1/2002 | Lechot | |
| 2002/0010470 A1 | 1/2002 | Lechot | |
| 2002/0099447 A1 | 7/2002 | Mears et al. | |
| 2002/0116067 A1 * | 8/2002 | Mears | A61B 17/00234 |
| | | | 623/22.4 |
| 2002/0193797 A1 | 12/2002 | Johnson et al. | |
| 2003/0004513 A1 | 1/2003 | Guzman et al. | |
| 2003/0018340 A1 | 1/2003 | Branch | |
| 2003/0050645 A1 | 3/2003 | Parker et al. | |
| 2003/0097135 A1 | 5/2003 | Penenberg | |
| 2003/0130741 A1 * | 7/2003 | McMinn | A61B 17/15 |
| | | | 623/23.14 |
| 2003/0158559 A1 * | 8/2003 | Diaz | A61B 17/1631 |
| | | | 606/91 |
| 2003/0181916 A1 | 9/2003 | Wolford | |
| 2003/0220696 A1 | 11/2003 | Mears et al. | |
| 2003/0229352 A1 * | 12/2003 | Penenberg | A61B 17/1746 |
| | | | 606/81 |
| 2003/0229356 A1 | 12/2003 | Dye | |
| 2003/0229357 A1 | 12/2003 | Dye | |

FOREIGN PATENT DOCUMENTS

| | | | |
|---|---|---|---|
| EP | 0357270 A1 | 3/1990 | |
| EP | 0470912 A2 | 2/1992 | |
| EP | 1149562 A2 | 10/2002 | |
| EP | 1149562 A3 | 1/2003 | |
| GB | 2372707 A | 9/2002 | |
| WO | WO 9738652 A1 * | 10/1997 | A61B 90/10 |
| WO | 03/057049 A1 | 7/2003 | |
| WO | 03/065906 A2 | 8/2003 | |

* cited by examiner

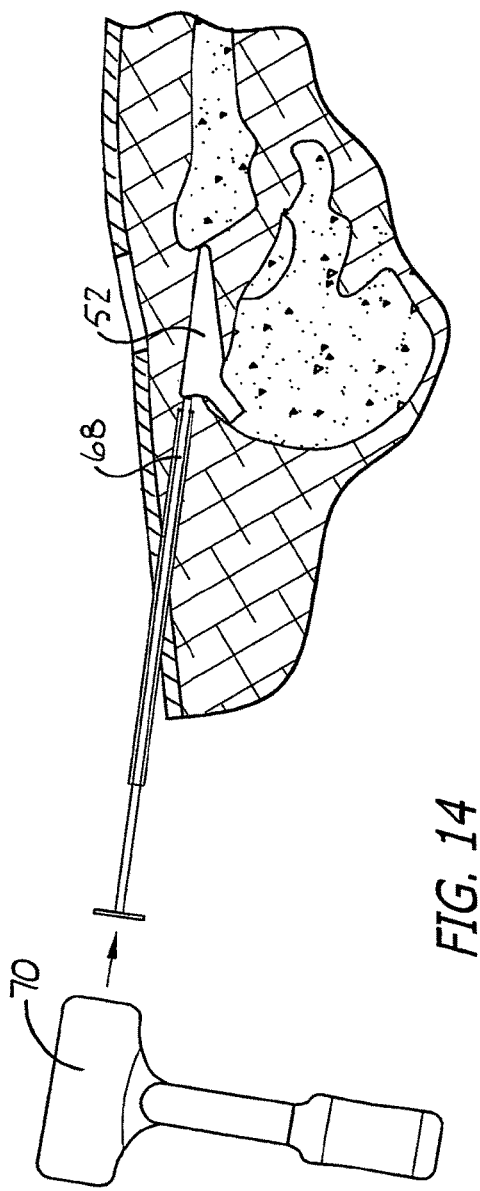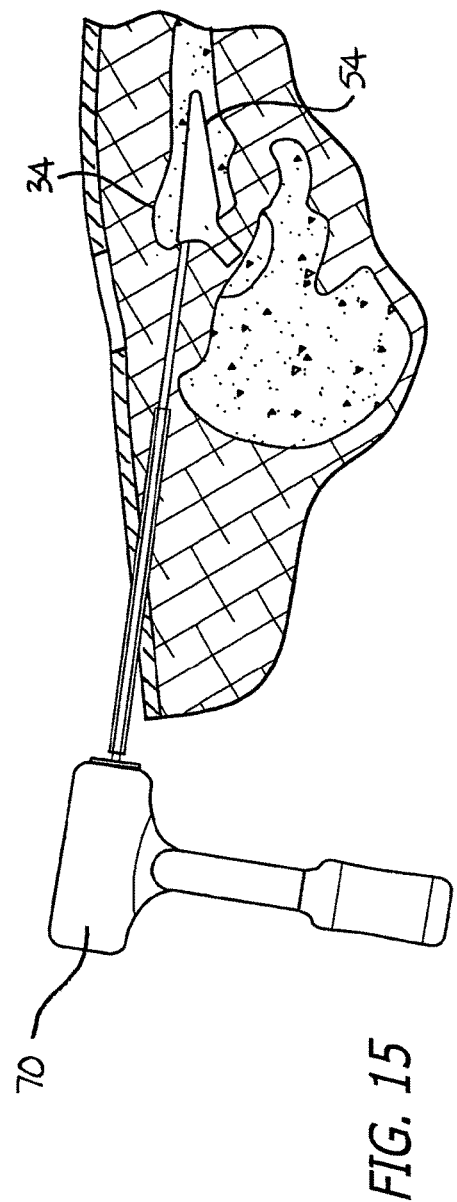
FIG. 14
FIG. 15

APPARATUS FOR AND METHOD OF PROVIDING A HIP REPLACEMENT

CROSS REFERENCE TO RELATED APPLICATIONS

This application is a continuation of and claims priority to: application Ser. No. 12/941,256, filed Nov. 8, 2010, which is a continuation of application Ser. No. 11/332,051, filed Jan. 13, 2006, which is issued as U.S. Pat. No. 7,833,229, which is a continuation of application Ser. No. 10/932,742, filed Sep. 1, 2004, which is issued as U.S. Pat. No. 6,997,928; application Ser. No. 10/683,008, filed Oct. 9, 2003, which is issued as U.S. Pat. No. 6,905,502; and application Ser. No. 10/166,209, filed Jun. 10, 2002 (the parent of application Ser. No. 10/683,008), which is abandoned, the entire disclosures of which are incorporated herein by reference.

STATEMENT REGARDING FEDERALLY SPONSORED RESEARCH OR DEVELOPMENT

Not applicable

REFERENCE TO A MICROFICHE APPENDIX

Not applicable

FIELD OF THE INVENTION

This invention relates to a method of providing a replacement for a patient's hip with a minimal loss of blood, minimal tissue trauma and a minimal length of operating time and patient recovery time. The invention also relates to a tool which is needed in the method constituting this invention.

BACKGROUND OF A PREFERRED EMBODIMENT OF THE INVENTION

Great progress has been made in the field of hip replacements. Considering that hip replacements may not even have existed a generation ago, hip replacements, particularly among the elderly, are now relatively common. In spite of the considerable progress which has been made, hip replacement operations are still relatively crude. For example, an incision of a relatively great length still has to be made in a patient's hip as one of the first steps in a hip replacement operation. The incision may be as long as approximately eight inches (8") to approximately twelve inches (12").

Such a large incision has caused patients to lose large amounts of blood and to suffer significant trauma. It has caused the length of the operation and the patient recovery time to be relatively long.

BRIEF DESCRIPTION OF A PREFERRED EMBODIMENT OF THE INVENTION

A minimal length main incision (e.g., approximately 1½"-3" long) and two portal incisions (each significantly less than 1" long) strategically displaced from the main incisions are provided in a patient's hip. A cannula is inserted through the portal incision to the acetabulum and a shaft is inserted through the cannula. A reamer is disposed through the main incision in the acetabulum and coupled to the shaft to ream the acetabulum when the shaft is rotated. Reamers of progressive size are then coupled to the shaft to progressively shape and size a socket in the acetabulum. An approximately hemispherical acetabular component is then disposed in the acetabulum to provide for hip rotation relative to the femur. The other portal (femoral portal) incision provides for a preparation of an insertion of a member into the patient's hip for preparing a femoral canal and then driving the' femoral stem into a cavity in the patient's femur.

The provision of the main incision and the portal incision.s minimizes the patient's loss of blood, tissue trauma, length of operating time and patient recovery time.

BRIEF DESCRIPTION OF THE DRAWINGS

In the drawings:

FIG. 14 is an enlarged fragmentary sectional view similar to that shown in FIG. 13 and shows how the femoral stem becomes disposed in the femur cavity; and FIG. 15 is an enlarged fragmentary sectional view similar to that shown in FIGS. 13 and 14 and shows the proper disposition of the femoral stem in the femur cavity.

DETAILED DESCRIPTION OF A PREFERRED EMBODIMENT OF THE INVENTION

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Figure 1:
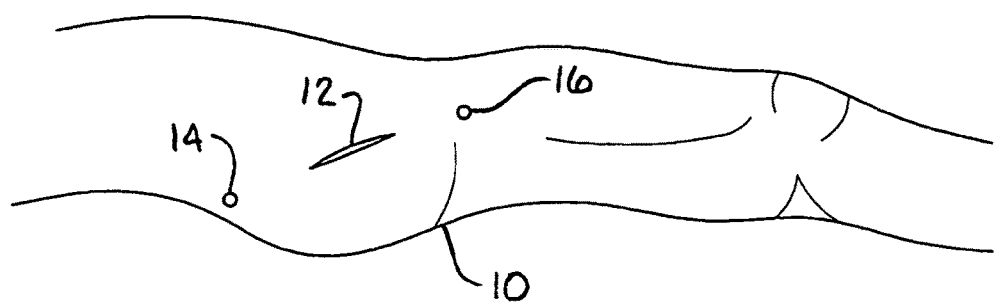
FIG. 1 is a fragmentary schematic side elevational view of a patient's hip and shows a main incision and portal incisions made in the patient's hip as an initial step in providing for a replacement of the patient's hip.

FIGS. 1-15 show progressive steps in performing a method constituting a preferred embodiment of the invention and also show apparatus included in the patentable features of the preferred embodiment of this invention. FIG. 1 schematically shows a patient's hip 10 and also shows a main incision 12 and a pair of portal incisions 14 and 16 may be an acetabular portal incision, may be on one side of the main incision and may be significantly less than one half inch (½") in length. As indicated in FIGS. 5-8 and 10-11, and as will be appreciated by those of skill in the art, the position of the acetabular portal incision 16 is selected to provide access to the acetabulum 22 in cooperation with the main incision 12 but without providing access to the patient's acetabulum 22 through the patient's femoral neck. The incision 14 may be a femoral incision, may be on the other side of the main incision 12 from the acetabular incision 16 and may also be significantly less than one half inch (½") in length. The portal incisions 14 and 16 may be of the same approximate length.

Figure 2:
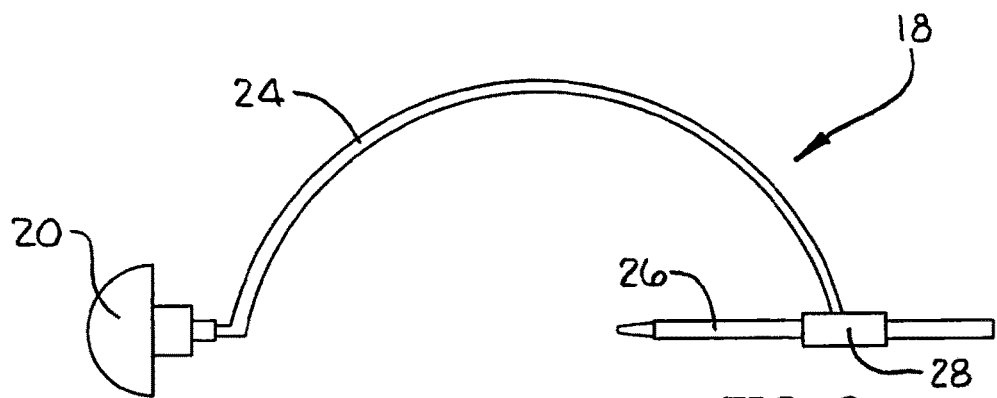
FIG. 2 is a side elevational view of a tool used by a surgeon to determine the positioning of the portal incisions in the patient's hip after the formation of the main incision in the patient's hip.

A tool generally indicated at 18 is shown in FIG. 2. The tool 18 may illustratively be used to locate the position of the portal incision 16. The tool 18 includes a positioning member 20 which may preferably have a hemispherical configuration to fit in an acetabulum 22 (FIG. 4) when the position of the acetabular portal incision 16 is being determined. A looped extension portion 24 extends from the positioning member 20. The portion 24 is preferably looped to extend through the main incision 12 to a position external to the patient's hip 10 and then to extend to a position approximating the position of the acetabular portal incision 16. It will be appreciated that the looped portion 24 may have a different configuration than that shown in FIG. 2 provided that the right end in FIG. 2 has a position corresponding substantially to that shown in FIG. 2. A marker member 26 such as a stylus attached to the looped portion at the right end of the looped portion 24 in FIG. 2. The marker member 26 is retained by a holder 28. As will be seen, the holder 28 and the marker member 26 have a substantially identical axial relationship with the positioning member 20.

Figure 3:
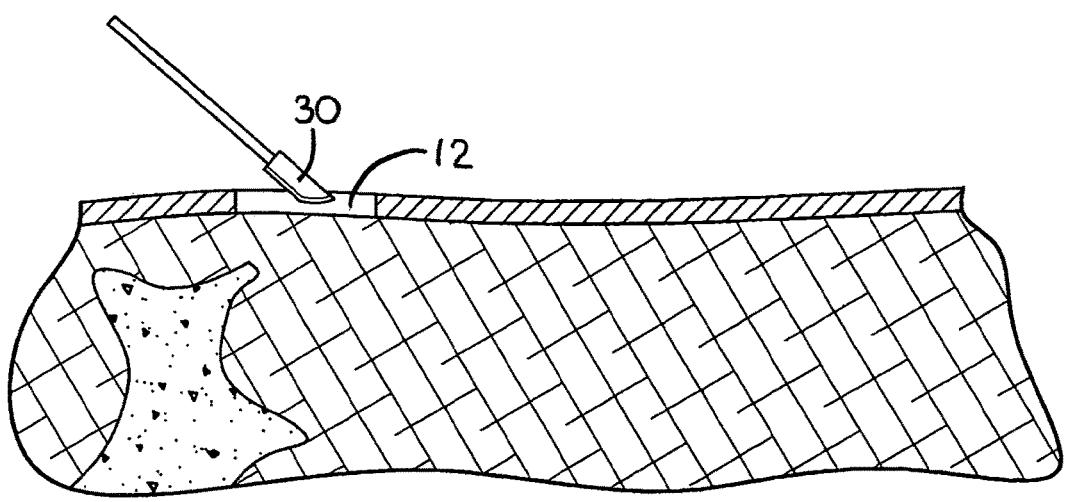
FIG. 3 is an enlarged fragmentary sectional view of a patient's hip and shows the formation of the main incision in the patient's hip.
Figure 4:
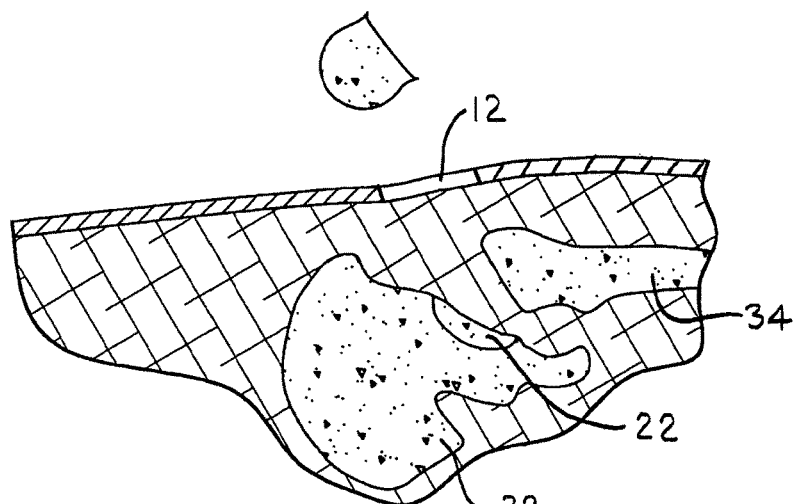
FIG. 4 is an enlarged fragmentary sectional view similar to that shown in FIG. 3 and shows the approximate positioning of the main incision in relation to a hip bone and a femur in the patient.

A first step in the performance of applicant's method is shown in FIG. 3. In this step, a cutter 30 is used to provide the main incision 12. This incision is preferably made anterior to, directly over or posterior to the greater trochanter. It will accordingly be appreciated that the positioning of the main incision 12 is somewhat discretionary. FIG. 4 is a somewhat schematic view showing the approximate positioning of the main incision 12 relative to the positioning of the patient's hip bone 32 and femur 34.

Figure 5:
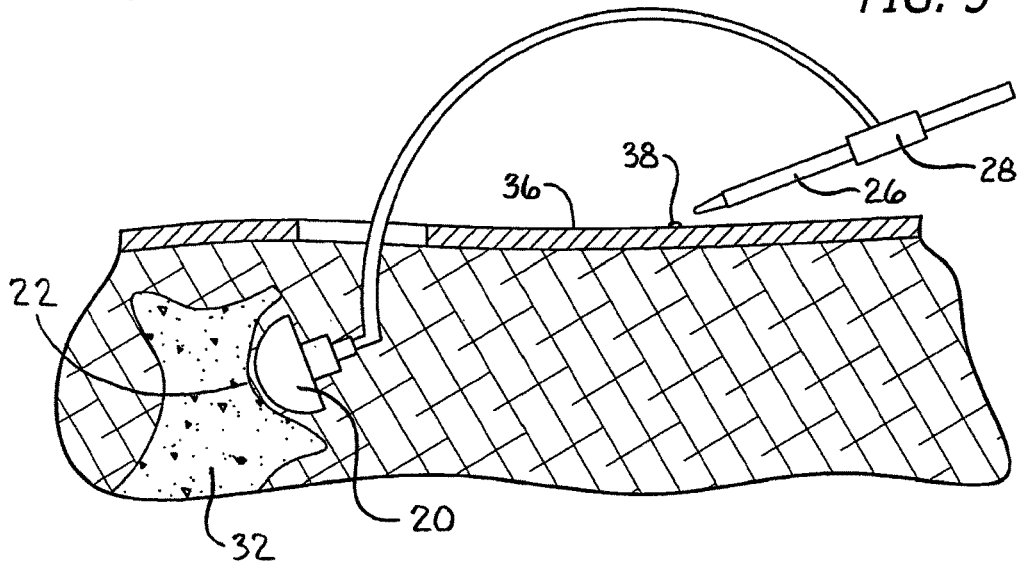
FIG. 5 is an enlarged fragmentary sectional view similar to that shown in FIG. 4 and shows the positioning of the tool of FIG. 2 in the patient's hip to determine the position of the portal incision for providing an acetabular shaping of the hip bone.
Figure 6:
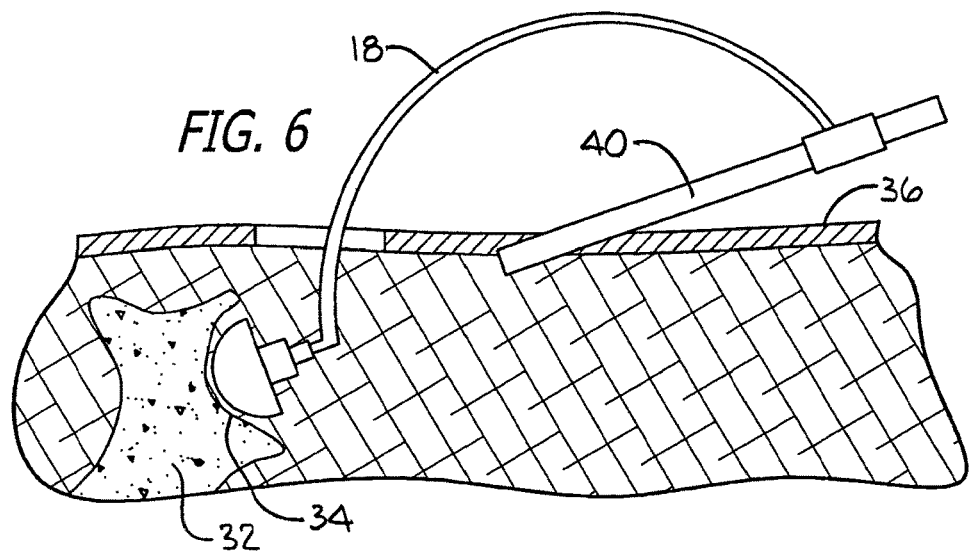
FIG. 6 is an enlarged fragmentary sectional view similar to that shown in FIG. 5 and shows partial insertion of a cannula into the patient's hip through the portal incision to provide for an acetabular shaping in the patient's hip.

FIG. 5 shows the hip bone 32 and the acetabulum 22 in the hip bone. FIG. 5 shows the disposition of the tool 18 with the positioning member 20 in the acetabulum 22. In this disposition, the marker member 26 abuts the patient's skin 36 in the region of the patient's hip and causes a mark 38 to be produced on the patient's skin. This mark indicates the position to be provided for the acetabular portal incision 16. FIG. 6 illustrates the positioning of a cannula 40 so that extends through the acetabular incision 16 at the mark 38 in the direction toward the axis of the positioning member 20. As indicated in FIGS. 5-8 and 10-11, and as will be appreciated by those of skill in the art, the cannula 40 communicates between the acetabular portal incision 16 and the acetabulum 22 without passing through the patient's femoral neck.

Figure 7:
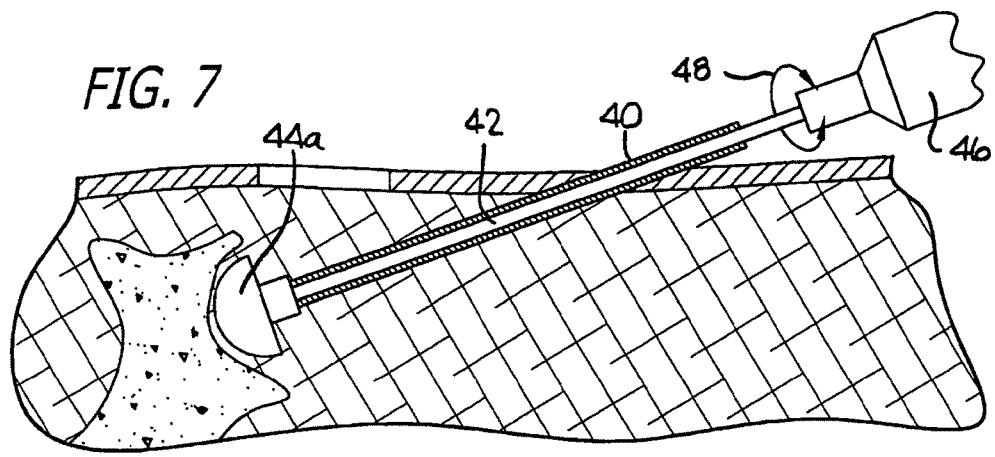
FIG. 7 is a fragmentary sectional view similar to that shown in FIGS. 5 and 6 and shows the positioning of a reamer through the cannula and the operation of the reamer to form the acetabulum in the patient's hip bone.
Figure 8:
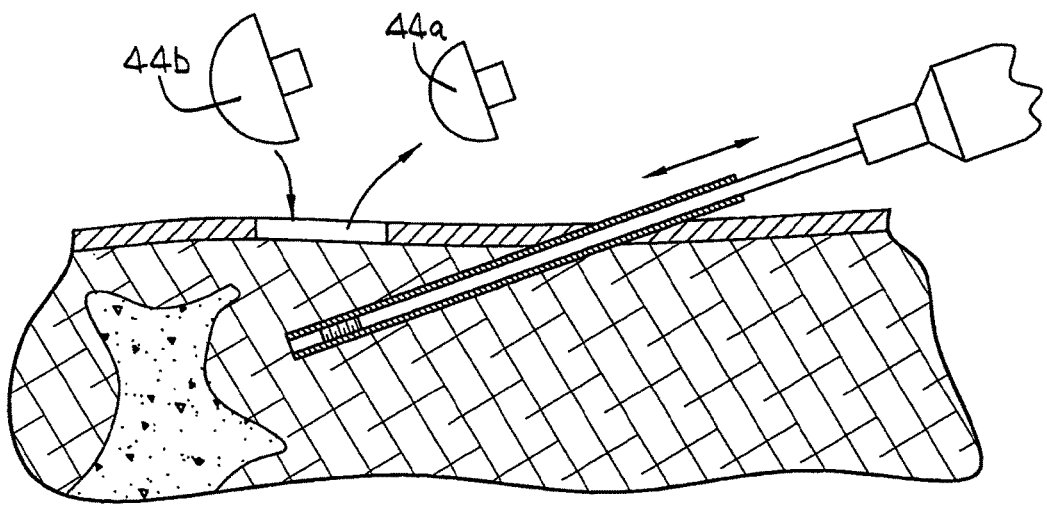
FIG. 8 is an enlarged fragmentary sectional view similar to that shown in FIGS. 5-8 and schematically shows the use of reamers of progressively increased size to shape the acetabulum in the patient's hip.
Figure 9:
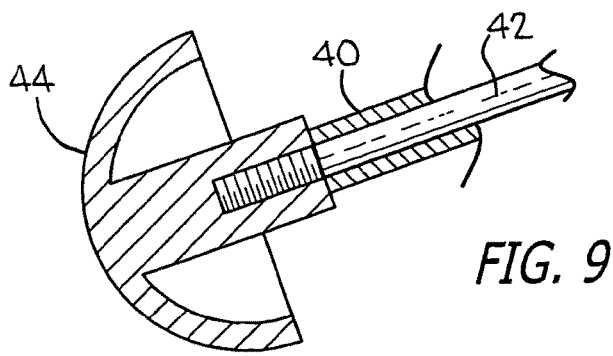
FIG. 9 is an enlarged fragmentary sectional view of one of the reamers shown in FIGS. 5-8.
Figure 10:
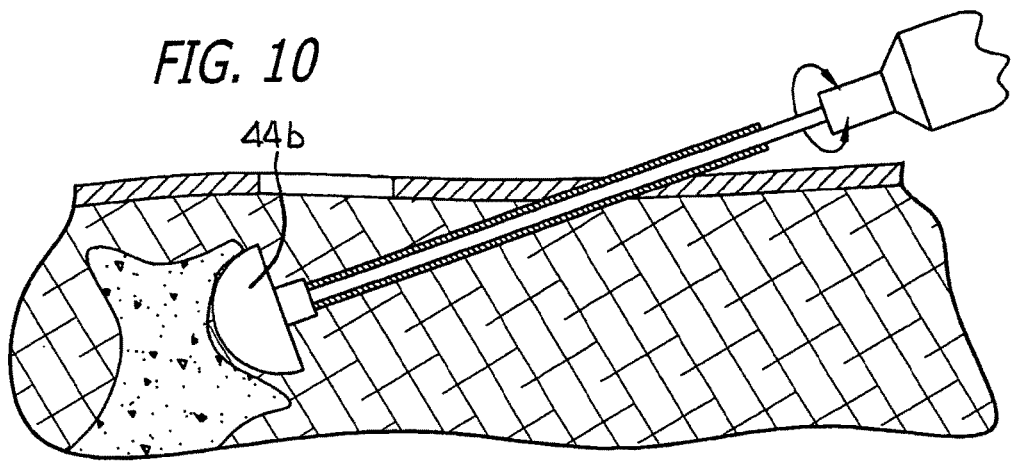
FIG. 10 is an enlarged fragmentary sectional view similar to that shown in FIG. 7 and shows a reamer which is large in comparison to the reamer shown in FIG. 7.
Figure 11:
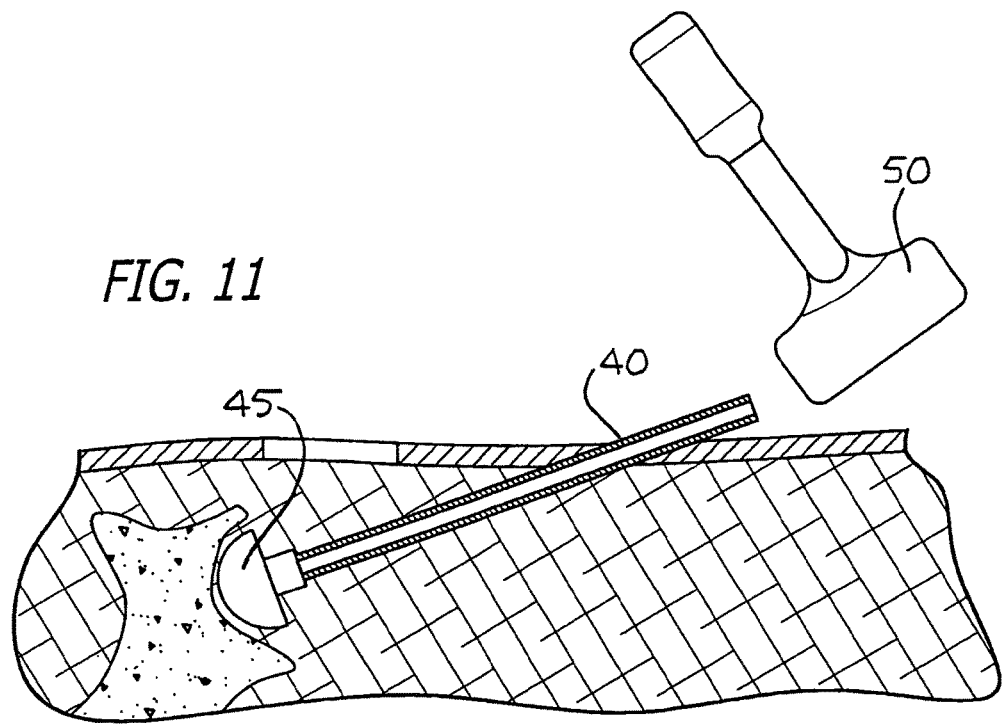
FIG. 11 is a fragmentary sectional view similar to that shown in FIGS. 5 and 6 and shows the insertion of an approximately hemispherical acetabular component into the acetabulum of the patient's hip to provide the pivotable relationship between the femoral ball and the acetabulum in the patient's hip bone.

FIG. 7 shows a shaft 42 extending through the cannula 40 and coupled to a reamer 44 which is disposed in the acetabulum 22. A motor 46 drives the shaft in one rotary direction to operate the reamer 44. The rotary movement of the shaft 42 is indicated at 48. As will be appreciated, the acetabulum 22 is sequentially reamed by reamers 44 of progressively increasing size. This is illustrated at 44a in FIG. 7 and at 44a and 44b in FIG. 8. It may also be seen by comparing the size of the reamers 44a and 44b respectively in FIGS. 7 and 10 and also in FIG. 8. When the acetabulum 22 has the desired shape, size and smoothness, a hemispherical shell (acetabular component or a trial component) 45 (FIG. 11) is introduced into the acetabulum 22 to provide a pivotal relationship with the femoral head. This may be accomplished by applying a mallet 50 to the shaft extending thru the cannula 40 as illustrated schematically at 50 in FIG. 11.

Figure 12:
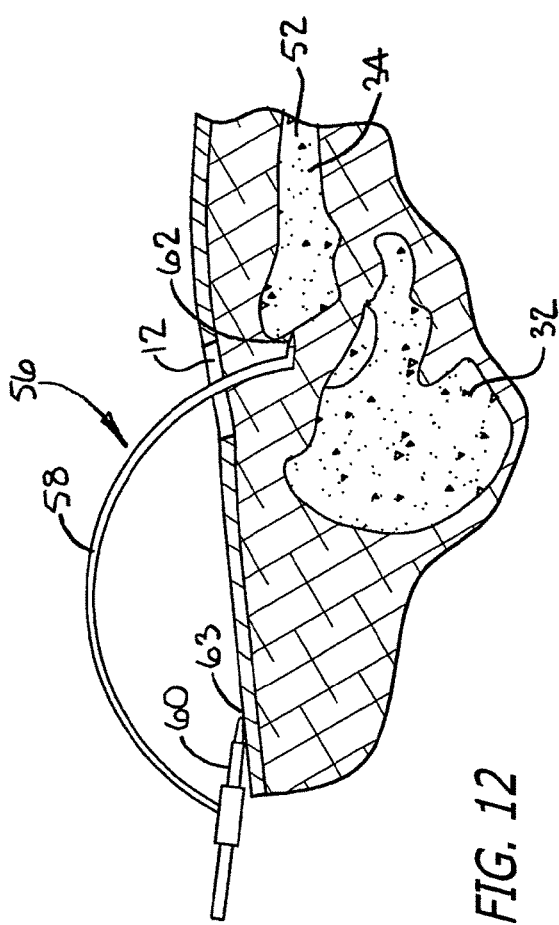
FIG. 12 is an enlarged fragmentary sectional view similar to that shown in FIG. 4 and shows the positioning relative to a femoral stem of a tool similar to that shown in FIG. 2 to determine the positioning of the portal for the femoral incision for obtaining the disposition of a femoral stem in a cavity in the patient's femur.
Figure 13:
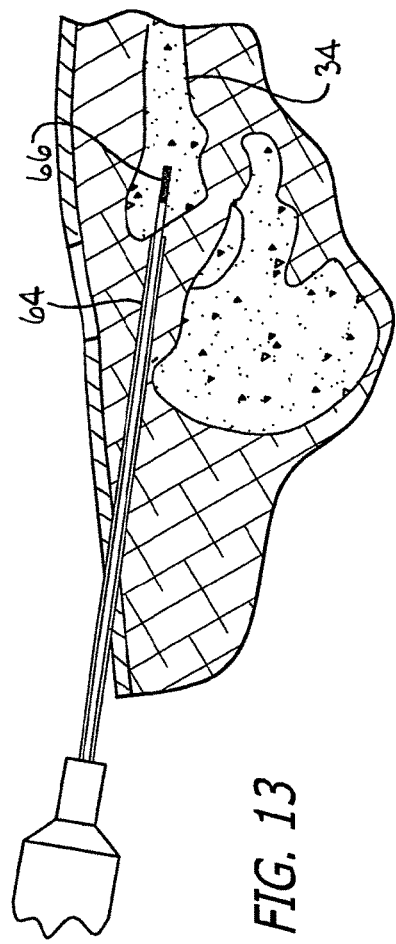
FIG. 13 is an enlarged fragmentary sectional view similar to that shown in FIG. 12 and shows the positioning of a cannula through the portal incision and the positioning of a rasp through the cannula to provide for the smoothing of the walls of the femur cavity.

FIGS. 12-15 relate to the formation of the femoral portal incision 14 and the use of this incision in connection with the disposition of the femoral stem 52 in a cavity 54 (FIG. 15) in the femur 34. As shown in FIG. 12, a tool generally indicated at 56 is provided to determine the position of the femoral portal incision 14. The tool 56 is similar in a number of respects to the tool 18. For example, the tool 56 may include an extension portion 58 and a marker member 60 respectively corresponding in configuration to the extension portion 24 and the marker member 26 in FIG. 2. The dimensions of the extension portion 58 may be different from those of the extension portion 24. The tool 56 may also be provided with a drive member 62 at the end opposite the marker member 60. The drive member 62 may have a finger configuration. The marker member 60 and the drive member 62 preferably are disposed on the same axis. When the drive member 62 is inserted into the main incision 12 and is disposed against the femoral stem 52, the marker member 60 makes a mark 63 a long scalpel blade may be passed thru this portal locator sleeve to indicate the position of the femoral portal incision 14 as shown in FIG. 12. A relatively long scalpel blade may then be passed through this portal locator sleeve.

A cannula 64 (FIG. 13) is then inserted through the femoral portal incision 14 to a position adjacent the femoral stem 32. If soft tissues permit, a cannula need not always be used. A rasp 66 or, a reamer, a drill or a tamp is passed through the cannula 64 into the cavity 54 in the femur 34 and is operated to prepare the walls of the cavity to receive the femur. In the claims, the term "rasp" is intended to include a reamer, drill or tamp or other suitable component. The rasp 66, or, a reamer, a drill or a tamp is then withdrawn from the cannula 64 and a drive member 68 (FIG. 14) is inserted through the cannula to abut the femoral stem. This is shown in FIG. 14. A mallet 70 in FIG. 15 is then applied against the drive member 68 to move the femoral stem 52 into the cavity 54 in the femur 34. This is shown in FIG. 15.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. A surgical method, comprising:
   inserting a positioning member of a first tool into a first incision, the first tool including an extension portion that extends from the positioning member at a first end to a holder at a second end;
   using the holder to mark a location for a second incision while the positioning member is disposed within an acetabulum;
   making the second incision based on the location identified by the holder; and
   inserting a cannula through the holder and into the second incision.

2. The surgical method of claim 1, wherein a length of the first incision is greater than a length of the second incision, and wherein a length of the second incision is less than about ½ inch.

3. The surgical method of claim 1, further comprising:
   feeding a rotatable shaft through the cannula;
   coupling a first reamer to a terminal end of the rotatable shaft, the first reamer being inserted through the first incision; and
   reaming the acetabulum using the first reamer.

4. The surgical method of claim 3, further comprising:
   inserting a second reamer into the first incision, wherein the second reamer is larger in size than the first reamer; and
   coupling the second reamer to the terminal end of the rotatable shaft.

5. The surgical method of claim 3, further comprising introducing an acetabulum component into the reamed acetabulum.

6. The surgical method of claim 1, further comprising:
   inserting a drive member of a second tool into the first incision, the second tool having an extension portion that extends from the drive member disposed at a third end to a second cannula disposed at a fourth end; and
   inserting the second cannula through a third incision while the drive member is disposed against a femoral stem.

7. The surgical method of claim 6, further comprising:
   inserting a rasp through the second cannula and into the third incision;
   preparing a cavity in a femur to receive a femoral stem using the rasp; and
   inserting the femoral stem into the cavity formed in the femur.

8. The surgical method of claim 7, wherein the rasp is one of a reamer, a drill, and a tamp.

9. The surgical method of claim 1, wherein the first incision is anterior to, directly over, or posterior to a greater trochanter of a patient.

10. A surgical method, comprising:
    making a first incision having a first length directly over, anterior to, or posterior to a greater trochanter of a patient;
    inserting a first end of a first tool into the first incision, the first tool extending from the first end to a second end that includes a holder;
    inserting a first cannula through the holder and into a second incision while the first end of the tool is disposed adjacent to an acetabulum of the patient,
    wherein a length of the first incision is greater than a length of the second incision, and wherein a length of the second incision is less than about ½ inch.

11. The surgical method of claim 10, further comprising:
    inserting a rotatable shaft through the first cannula;
    coupling a reamer to a terminal end of the rotatable shaft; and
    reaming the acetabulum using the reamer.

12. The surgical method of claim 11, further comprising:
    inserting a second reamer into the first incision, wherein the second reamer is larger in size that the first reamer; and
    coupling the second reamer to the terminal end of the rotatable shaft.

13. The surgical method of claim 11, further comprising introducing an acetabulum component into the reamed acetabulum through the first incision.

14. The surgical method of claim 10, wherein the first tool includes a curved extension that extends from the first end to the second end such that first end is axially aligned with the second end.

15. The surgical method of claim 10, further comprising:
    inserting a first end of a second tool into the first incision, the second tool having a curved extension that extends to a second end that includes a second cannula; and
    inserting the second cannula through a third incision when the first end of the second tool is disposed against a femoral stem.

16. The surgical method of claim 15, further comprising:
    inserting a rasp into the second cannula;
    preparing a cavity in a femur sized and configured to receive a femoral stem using the rasp; and
    inserting the femoral stem into the cavity formed in the femur.

17. A surgical method, comprising:
    inserting a first end of a first tool into a first incision made in a hip of a patient, the first tool including a curved portion that extends to a second end that includes a first holder that is axially aligned with the first end;
    inserting a first cannula through the holder and into a second incision;
    inserting a first end of a second tool into the first incision, the second tool including a curved portion that extends to a second end that includes a second holder that is axially aligned with the first end of the second tool; and
    inserting a second cannula through the second holder and into a third incision
    wherein a length of the first incision is greater than a length of the second incision, and wherein a length of the second incision is less than about ½ inch.

18. The surgical method of claim 17, further comprising:
    inserting a rotatable shaft through the first cannula;
    coupling a reamer to an end of the rotatable shaft; and
    reaming the acetabulum using the reamer.

19. The surgical method of claim 17, further comprising introducing an acetabulum component into an acetabulum through the first incision.

20. The surgical method of claim 17, further comprising:
    inserting a rasp through the second cannula and into the third incision;

preparing a cavity in a femur sized and configured to receive a femoral stem using the rasp; and inserting the femoral stem into the cavity formed in the femur.

* * * * *